(12) United States Patent
Gelbwachs

(10) Patent No.: US 7,067,812 B2
(45) Date of Patent: Jun. 27, 2006

(54) MULTISPECTRAL SELECTIVE REFLECTIVE LIDAR

(75) Inventor: Jerry A. Gelbwachs, Hermosa Beach, CA (US)

(73) Assignee: The Aerospace Corporation, El Segundo, CA (US)

(*) Notice: Subject to any disclaimer, the term of this patent is extended or adjusted under 35 U.S.C. 154(b) by 0 days.

(21) Appl. No.: 10/974,224

(22) Filed: Oct. 27, 2004

(65) Prior Publication Data

US 2006/0086902 A1    Apr. 27, 2006

(51) Int. Cl.
*G01J 5/02*    (2006.01)
*G01J 3/45*    (2006.01)
*G01N 21/00*    (2006.01)

(52) U.S. Cl. .................. 250/339.12; 356/433; 356/455

(58) Field of Classification Search ........... 250/339.01, 250/339.06, 339.12
See application file for complete search history.

(56) References Cited

U.S. PATENT DOCUMENTS

| | | | | |
|---|---|---|---|---|
| 3,788,742 | A * | 1/1974 | Garbuny | 356/5.03 |
| 5,015,099 | A * | 5/1991 | Nagai et al. | 356/437 |
| 5,652,717 | A * | 7/1997 | Miller et al. | 703/6 |
| 2003/0227628 | A1* | 12/2003 | Kreimer et al. | 356/419 |

OTHER PUBLICATIONS

Brown L.R. et al, Methane Line Parameters in HITRAN, May 2003, Journal of Quantitative Spectroscopy and Radiative Transfer, vol. 82 Issues 1-4, pp. 219-238.*
Collings M.P. et al, Laboratory Studies of the Interaction of Carbon Monoxide with Water Ice, Sep. 2003, Astrophysics and Space Science, vol. 285 No. 3-4, pp. 633-659.*
Gerakines P.A. et al, Carbon Suboxide in Astrophysical Ice Analogs, Dec. 2001, Icarus, vol. 154 Issue 2, pp. 372-380.*
Wong M.H. et al, Identification of the 10-μm Ammonia Ice Feature on Jupiter, Apr.-May 2004, Planetary and Space Science, vol. 52 Issues 5-6, pp. 385-395.*
Cvijin P.V. et al, Reflectance Spectra of Terrestrial Surface Materials at CO2 Laser Wavelengths: Effects on DIAL and Geological Remote Sensing, Oct. 1987, Applied Optics, vol. 26 No. 19, pp. 4323-4329.*

* cited by examiner

*Primary Examiner*—David Porta
*Assistant Examiner*—David S. Baker
(74) *Attorney, Agent, or Firm*—Derrick Michael Reid

(57) ABSTRACT

A multispectral selective reflection Lidar system generates alternating pulses of at least two wavelengths and senses returns for determining the presence of a predetermined material absorbing and reradiating one wavelength as selective reflections, but not the other. A detector can readily determine the presence or absence or an absorbing and reradiating return. The system is for preferred use as an orbiter sensor about a planetary body, such as a Jupiter moon, for determining the presence of organic material and for the relay of information back to earth.

7 Claims, 3 Drawing Sheets

METHOD OF DETECTING AN ABSORBING AND RADIATING REMOTE MATERIAL

ABSORPTION SPECTRUM

RADIATION REFLECTION SPECTRUM

MODULATED LASER OUTPUT

DETECTOR OUTPUT WITHOUT ABSORPTION

DETECTOR OUTPUT WITH ABSORPTION

METHOD OF DETECTING AN ABSORBING AND RADIATING REMOTE MATERIAL

MULTISPECTRAL SELECTIVE REFLECTIVE LIDAR

STATEMENT OF GOVERNMENT INTEREST

The invention was made with Government support under contract No. F04701-00-C-0009 by the Department of the Air Force. The Government has certain rights in the invention.

FIELD OF THE INVENTION

The invention relates to the field of surface chemical analysis. More particularly, the present invention relates to remote surface chemical analysis using spectral selective reflective Lidar.

BACKGROUND OF THE INVENTION

Laser illuminating detection and ranging (Lidar) systems have been used for remote sensing. Typically, a Lidar system illuminates a remote material. The remote material absorbs, transmits, or reflects illuminating signals. For differential absorption, the Lidars illuminate a diffuse gaseous material for chemical characterization where the Lidar illumination has two wavelengths, where one wavelength is absorbed and other is not, such that, a weaker return at the absorption wavelength will indicate the presence of the remote diffuse gaseous material. For conventional ranging, the Lidar illuminates a remote material and detects reflected returns. A Fresnel reflection, that is, an ordinary reflection, returns a small portion of the Lidar illumination. The presence of returns indicates that a reflecting material is present. The absence of returns indicates that a remote reflecting material has not been illuminated. The ranging Lidar system detects the presence or absence of returns for indicating the absence or presence of the remote ordinary reflecting material, respectively, using ordinary reflection returns for ranging, and not surface material characterization. A Lidar can be used as part of an instrument package for surface chemical characterization. Surface chemical characterization can be used on space probes orbiting distant and frozen worlds. For example, a space flight is being planned by NASA to go to three moons of Jupiter, including Callisto, Ganymede, and Europa. These moons have been selected for investigation because these moons appear to have the ingredients considered essential for life. The surface temperatures of these moons are cold so that common materials occur in the frozen form. A surface chemical characterization Lidar could be used for a mission to Jupiter as an icy moon orbiter. A priority science goal of the icy moon orbiter mission is to scout the potential for sustaining life. Identification and mapping of the surface constituents would provide important data towards this goal. Traditional means of surface characterization from orbit rely upon high-resolution spectral analysis of reflected sunlight or surface thermal emission. Because of the distant position from the sun to Jupiter, the moons receive little sunlight prohibiting analysis of sun reflections. Further, the low surface temperatures of the moons provide insufficient thermal radiation for high-resolution spectral analysis. These and other disadvantages are solved or reduced using the invention.

SUMMARY OF THE INVENTION

An object of the invention is to provide a method for sensing a remote surface material using selective reflections of Lidar illuminations.

Another object of the invention is to provide a method for sensing a remote surface material that firstly absorbs a Lidar illumination and then secondly reradiates the absorbed illumination, as wavelength selective reflected returns.

Yet another object of the invention is to provide a method for sensing a remote surface material that selectively reflects the Lidar illumination as selective reflections that are detected.

Still another object of the invention is to provide a method for illuminating a remote surface material with at least two different, first and second, wavelengths for sensing a remote surface material that selectively reflects the first wavelength illumination that is detected, where the second wavelength is not absorbed nor reflected as a selective reflective return so that a difference between the returns of the first and second wavelength indicates the presence of the remote surface material.

The invention is directed to a remote surface material detecting Lidar system that relies upon absorption and reradiation, that is, selective reflection, of laser pulses having predetermined wavelength. In the preferred form, the Lidar generates alternating pulses of two wavelengths, the first of which is absorbed and reradiated, the second which is neither substantially absorbed and reradiated or reflected. The detecting these selective reflected returns of the absorbed and reradiated laser pulses indicates the presence of remote surface material. These and other advantages will become more apparent from the following detailed description of the preferred embodiment.

DETAILED DESCRIPTION OF THE PREFERRED EMBODIMENT

Figure 1A:
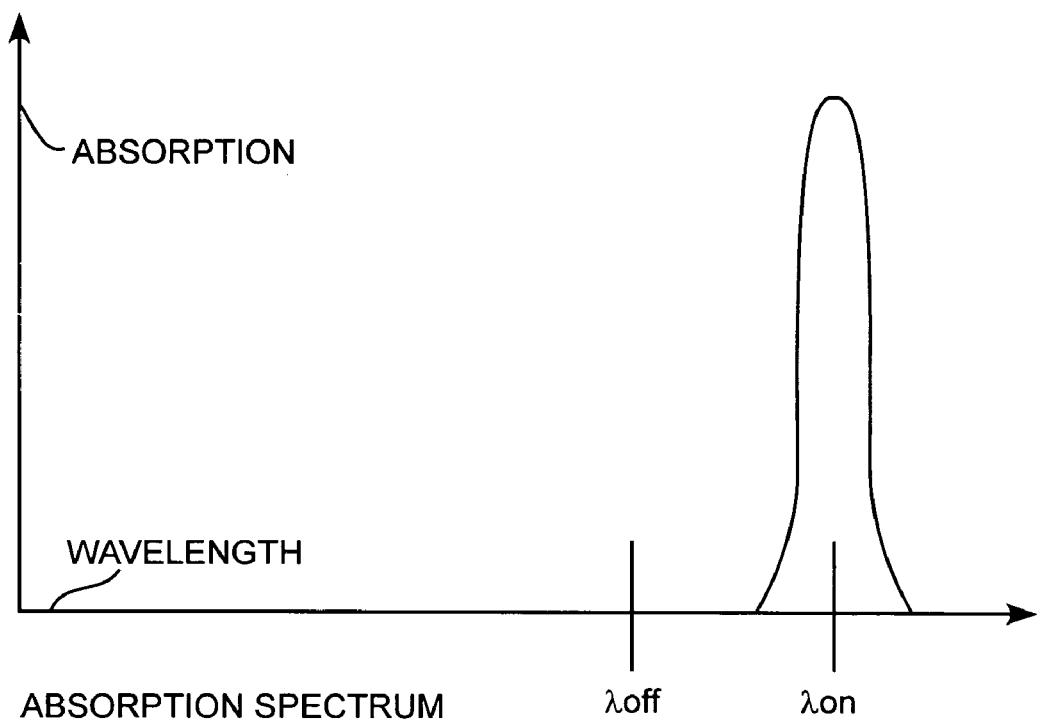
FIG. 1A is a plot a Lidar illumination by alternating $\lambda$on and $\lambda$off wavelengths.
Figure 1B:
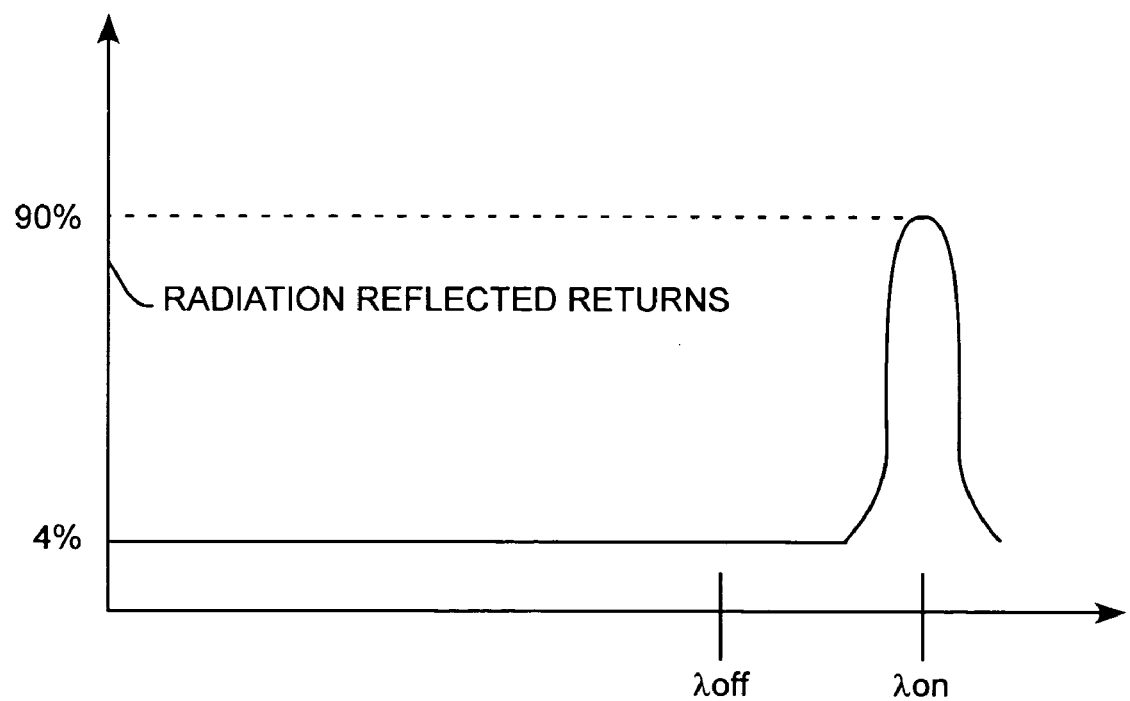
FIG. 1B is a plot a Lidar return at the $\lambda$on wavelength.
Figure 2A:
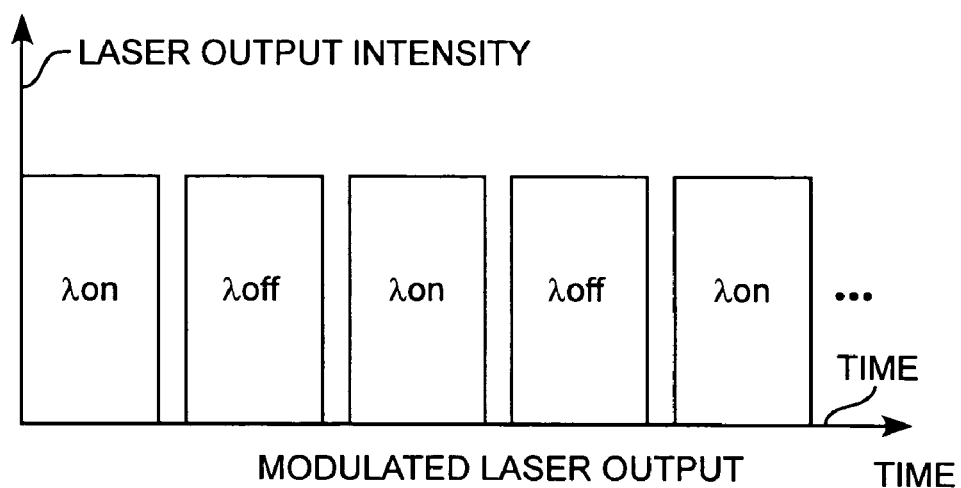
FIG. 2A is a pulse train of laser pulses.
Figure 2B:
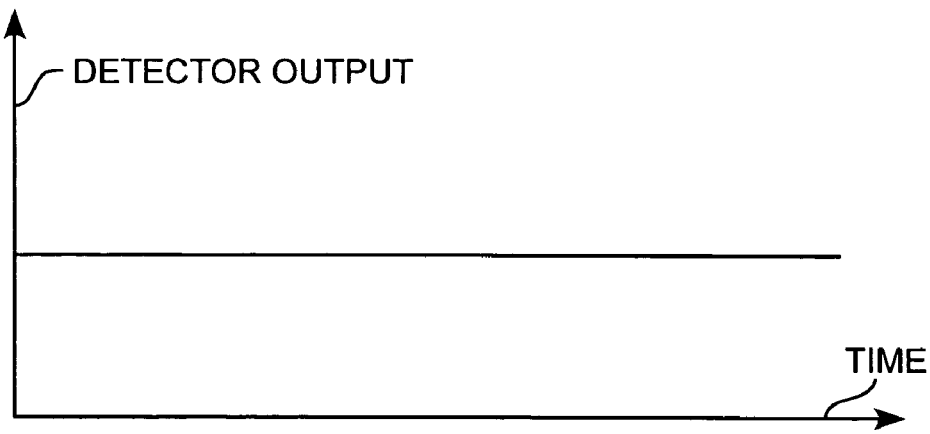
FIG. 2B is a plot of a detector output without surface absorption.
Figure 2C:
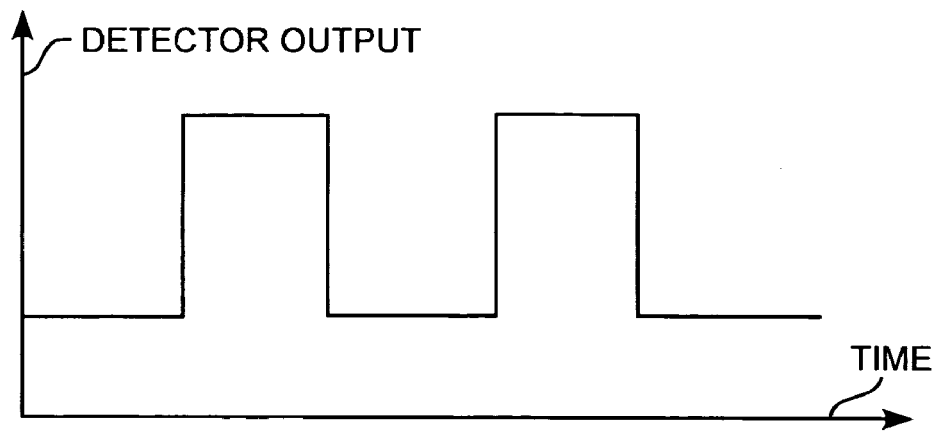
FIG. 2C is a plot of a detector output with surface absorption.

An embodiment of the invention is described with reference to the figures using reference designations as shown in the figures. A remote sensing surface chemical analysis instrument includes a Lidar for generating laser pulses and a detector for detecting returns. Referring to FIGS. 1A and 1B, the Lidar generates at least one laser pulse at a first $\lambda$on wavelength towards a surface material. When the first wavelength $\lambda$on is not absorbed and hence not reradiated by the surface material, there are insignificant first wavelength $\lambda$on ordinary reflected returns. The insignificant returns can be small Fresnel reflections. When the first wavelength $\lambda$on is absorbed and reradiated as selective reflections, then there is a large return at the first wavelength $\lambda$on. Referring to FIGS. 1A, 1B, 2A, 2B, and 2C, the preferred Lidar system generates alternating pulses at the first wavelength $\lambda$on and a second wavelength $\lambda$off. When the first wavelength $\lambda$on and the second wavelength $\lambda$off are not absorbed and hence not reradiated by the surface material, there are equally insignificant first wavelength $\lambda$on returns and insignificant second wavelength return $\lambda$off. When the first wavelength $\lambda$on is absorbed and reradiated as selective reflections, and the second wavelength λoff is not, then there is an alternating large reflection return at the first wavelength λon, as compared to the second wavelength return λoff. A return photodetector can be used to generate a detector output. The detector output is a null level indicating no returns and hence no absorption and reradiation. The comparison detection of returns from both wavelengths eliminates noise or false returns. When the first wavelength λon is absorbed and then returned and the second wavelength doff is not, the detector output oscillates between high and low. The difference between a level detector output and an oscillating output can be easily differentiated. Hence, the detector output of Lidar returns is used for indicating the presence of the surface material that absorbs and reradiates the first wavelengths λon, but not the second wavelength λoff. As such, the remote surface sensing Lidar system is a multispectral selective reflection Lidar.

Figure 3:
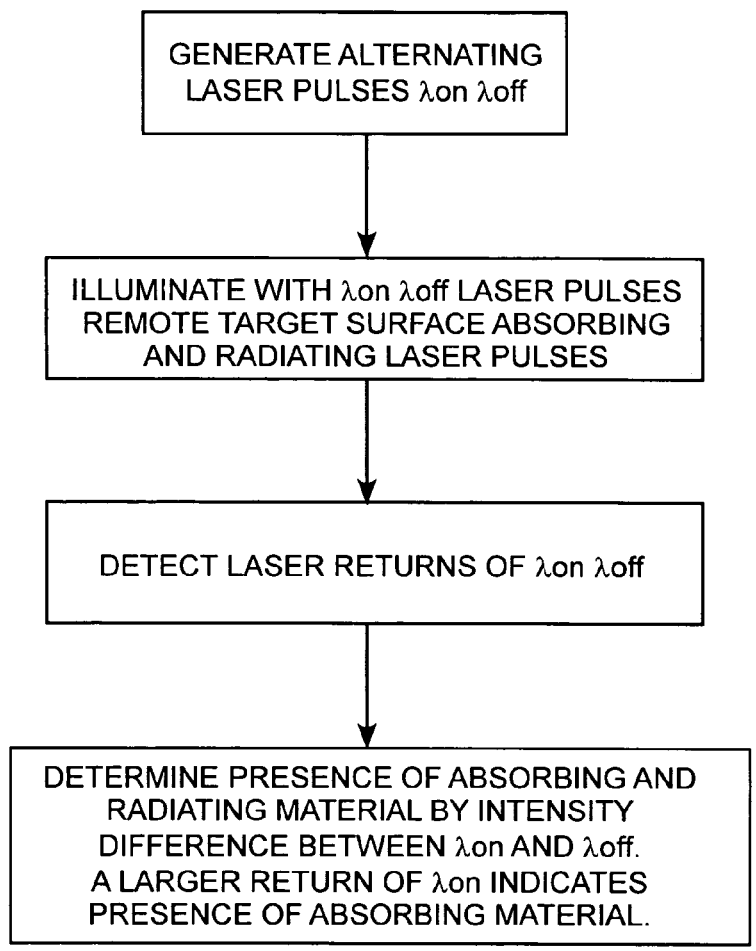
FIG. 3 is a process flow of a method of detecting an absorbing and radiating remote surface material.

Referring to FIG. 3, a Lidar system generates alternating λon and λoff pulses. The λon and λoff pulses illuminate a surface attempting to sense the presence of a predetermined material that will selectively reflect the first wavelength λon but not the second wavelength doff. The first and second wavelength returns are detected for determining the presence of the predetermined materials. The return photodetector can generate a constant electronic level output when the first and second wavelengths are equally returned, or generate an alternating output when the first wavelength return is greater that the second wavelength return.

In the preferred form, this multispectral selective reflection Lidar system relies upon a 3 to 11 μm spectral region containing absorption bands useful for the selective identification of the compounds of interest. For example, characteristic strong absorption peaks for frozen $CH_4$, CO, $CO_2$, and $NH_3$, occur at 1031/cm, 2139/cm, 2345/cm, and 3376/cm, respectively. The Lidar system can be used to predetermined species identification. The multispectral selective reflection Lidar system combines scanning IR multispectral imager and a variant of differential absorption IR Lidar. The multispectral selective reflection Lidar instrument can have six components including an IR illuminator, a scanner to direct the IR radiation onto the surface, a collection telescope, a spectral dispersive element, a photo detector array, and signal processing electronics. These are conventional components well known by those skilled in the art. There are many physical embodiments that can be realized to implement the detection method.

The IR illuminator generates two or three wavelengths that are selected for each compound of interest. The first wavelength λon coincides with a strong characteristic absorption feature of the compound while the second wavelength λoff is positioned at a spectrally nearby absorption minimum. Another wavelength λoff could be used to reduce ambiguity for species with overlapping spectra. Well-separated absorptions can be confined to two wavelengths. The typical wavelength separation between first and second wavelengths is less than 10/cm.

Return signals at such closely spaced IR wavelengths may not be separated readily by conventional IR filters. There are several different modulation schemes to differentiate returns at closely spaced wavelengths that do not require spectrally selective elements and permit the use of a single photo detector. For example, one implementation could use a small separate laser that emits each wavelength. The lasers are modulated 180° out of phase with respect to each other. After a roundtrip to the surface of a moon, for example, both wavelengths are incident upon the same photo detector. Each wavelength will be equally reflected and produce a dc photo response in the absence of the species of interest. In the presence of the species of interest, the first wavelength λon signal will be significantly enhanced due to selective reflection resulting in an imbalance in the reflected light. Selective reflection is a well-known method of molecular characterization of crystals in the IR-FIR spectral region in the laboratory. The selective reflection produces an ac component in the photo response that serves to indicate the presence of the compound using phase-sensitive detection. Hence, for N species there will be a 2N laser array operating continually. Hence, the Lidar system is a remote sensing Lidar that employs the principle of selective reflection A scanner unit can be used to take the collimated laser emissions and scans those emissions over the surface of the moon in a cross track pattern. The satellite orbiter motion provides along track coverage. A collection telescope could be pointed toward the surface of the moon to collect simultaneously the reflected laser light at each of the 2N wavelengths. The collection telescope will direct the light to dispersive device. The collector remains fixed having a field-of-view encompasses many spot sizes in the cross track direction. The size of each spot is predetermined to yield the requisite spatial resolution. A dispersive element can be used to collect light that will pass through a dispersive device, such as an IR prism where the individual wavelength pairs will be spatially separated from each other, when each wavelength pair cannot be resolved spatially. A photo detector array can be used to detect returns. The dispersive IR returns should be focused onto the photo detector array where the light is converted into electronic pulses. The photo detector array should be designed so that each of the 2N wavelengths is resolved and impinges upon a different pixel in one dimension. The images of the individual spots on the ground comprise the other array dimension. Signal processing electronics can be used to enhance return detection. The signal processing electronics can take the output of the IR photo detector array and convert the output into a format that can be assimilated by the spacecraft data relay system for transmission to the Earth. Various levels of signal processing may occur before transmission using various algorithms that relate array output signals to surface chemical compounds.

The present invention is directed to sensing absorbed and reradiated returns for a surface material from a remote Lidar system. The method preferably employs selective reflections to remotely determine surface chemical composition using at least two different wavelengths. The preferred form uses a modulation scheme for the use of continuous wave laser sources in the application of remote selective reflection measurements for λon wavelength and λoff wavelength separation of less than 1% that allows the use of a single photo detector. The combination of remote selective reflection and a detector array can be used for spatially resolved surface chemical characterization. The system could be used for detecting surface materials on Jupiter's icy moons, including Callisto, Ganymede, and Europa. The method can be used for scientific missions to survey remotely the surface of the moons in search of organic compounds, or used for high-resolution spectral analysis as a standard method for remote surface characterization, using various system implementations. Those skilled in the art can make enhancements, improvements, and modifications to the invention, and these enhancements, improvements, and modifications may nonetheless fall within the spirit and scope of the following claims.

What is claimed is:

1. A method for determining the presence of a predetermined surface material on a planetary body, the method comprising the steps of,
generating a laser pulse at a first wavelength, the first wavelength being at an absorption band peak of an absorption band of the predetermined surface material, the absorption band absorbing the first wavelength and reradiating the first wavelength as selective reflection first returns,
illuminating the planetary body with the first wavelength,
detecting first returns from the planetary body, the first returns being the selective reflection first returns of the first wavelength,
generating a laser pulse at a second wavelength, the second wavelength being outside the absorption band of the predetermined surface material, the absorption band not absorbing the second wavelength and not reradiating the second wavelength,
illuminating the planetary body with the second wavelength, and
detecting second returns from the planetary body, the second returns being returns of the second wavelength, and
determining the presence of the material on the surface of the planetary body by comparing the first and second returns to each other, the first returns being greater than the second returns as the first returns are reradiated by the predetermined surface material and the second returns are not reradiated by the predetermined surface material.

2. The method of claim 1 wherein,
the planetary body is a moon of Jupiter.

3. The method of claim 1 further comprising the step of,
propagating the first wavelength through space.

4. The method of claim 1 wherein,
the surface material is selected from the group consisting of $CH_4$, $CO$, $CO_2$, and $NH_3$, and the first wavelength selected from the group consisting of 1031/cm, 2139/cm, 2345/cm, and 3376/cm, respectively.

5. The method of claim 1 wherein,
the difference between the first wavelength and the second wavelength is less than one percent.

6. The method of claim 1 wherein,
the predetermined surface material is present on the planetary body when the first returns are larger than the second returns.

7. A method for determining the presence of a predetermined surface material on a planetary body, the method comprising the steps of,
generating a laser pulse at a first wavelength, the first wavelength being at an absorption band peak of an absorption band of the predetermined surface material, the absorption band absorbing the first wavelength and reradiating the first wavelength as selective reflection first returns,
illuminating the planetary body with the first wavelength,
detecting first returns from the planetary body, the first returns being the selective reflection first returns of the first wavelength,
generating a laser pulse at a second wavelength, the second wavelength being outside the absorption band of the predetermined surface material, the absorption band not absorbing the second wavelength and not reradiating the second wavelength,
illuminating the planetary body with the second wavelength, and
detecting second returns from the planetary body, the second returns being returns of the second wavelength as ordinary reflections, and
determining the presence of the material on the surface of the planetary body by comparing the first and second returns to each other, the first returns being greater than the second returns as the first returns are reradiated by the predetermined surface material and the second returns are not reradiated by the predetermined surface material.

* * * * *